United States Patent
Lesaffre et al.

(10) Patent No.: US 11,344,821 B2
(45) Date of Patent: May 31, 2022

(54) CHROMATOGRAPHIC SEPARATION OF AMMONIUM SULFATE AND 2-HYDROXY-2-METHYLPROPIONIC ACID

(71) Applicant: TRINSEO EUROPE GMBH, Horgen (CH)

(72) Inventors: Thibault Lesaffre, Caluire et Cuire (FR); Marjory Edon, Saint-Jean d'Ardieres (FR); Laurine Redelsperger, Meyzieu (FR); Aymeric Duplessix, Lyons (FR)

(73) Assignee: TRINSEO EUROPE GMBH, Horgen (CH)

( * ) Notice: Subject to any disclaimer, the term of this patent is extended or adjusted under 35 U.S.C. 154(b) by 0 days.

(21) Appl. No.: 16/978,882

(22) PCT Filed: Mar. 7, 2019

(86) PCT No.: PCT/FR2019/050506
§ 371 (c)(1),
(2) Date: Sep. 8, 2020

(87) PCT Pub. No.: WO2019/171004
PCT Pub. Date: Sep. 12, 2019

(65) Prior Publication Data
US 2021/0046400 A1  Feb. 18, 2021

(30) Foreign Application Priority Data
Mar. 9, 2018 (FR) .................. FR18.52067

(51) Int. Cl.
*C07C 69/01* (2006.01)
*B01D 15/18* (2006.01)
*B01D 15/36* (2006.01)
*C07C 67/48* (2006.01)

(52) U.S. Cl.
CPC ....... *B01D 15/185* (2013.01); *B01D 15/1864* (2013.01); *B01D 15/365* (2013.01); *C07C 67/48* (2013.01); *B01D 2257/306* (2013.01); *B01D 2257/406* (2013.01); *C07C 69/01* (2013.01)

(58) Field of Classification Search
CPC ....... C07C 67/48; C07C 69/01; B01D 15/185; B01D 15/1864; B01D 15/365; B01D 2257/306; B01D 2257/406
See application file for complete search history.

(56) References Cited

U.S. PATENT DOCUMENTS

| | | | |
|---|---|---|---|
| 4,015,946 A | 4/1977 | Bonnema et al. | |
| 4,981,794 A | 1/1991 | Robison et al. | |
| 2012/0329096 A1 | 12/2012 | Foody et al. | |
| 2016/0326112 A1* | 11/2016 | Brichant | C07D 233/64 |

FOREIGN PATENT DOCUMENTS

| | | | | |
|---|---|---|---|---|
| CA | 486040 | * | 8/1952 | |
| GB | 578307 | * | 6/1946 | B01J 41/13 |

* cited by examiner

*Primary Examiner* — Yate' K Cutliff
(74) *Attorney, Agent, or Firm* — RatnerPrestia

(57) ABSTRACT

The invention relates to a process for the chromatographic purification of a starting stream containing ammonium sulfate and 2-hydroxy-2-methylpropionic acid, comprising:
  passage of the starting stream through a bed of stationary phase;
  elution of a raffinate enriched in ammonium sulfate and depleted in 2-hydroxy-2-methylpropionic acid; and
  elution of an extract enriched in 2-hydroxy-2-methylpropionic acid and depleted in ammonium sulfate.

19 Claims, 1 Drawing Sheet

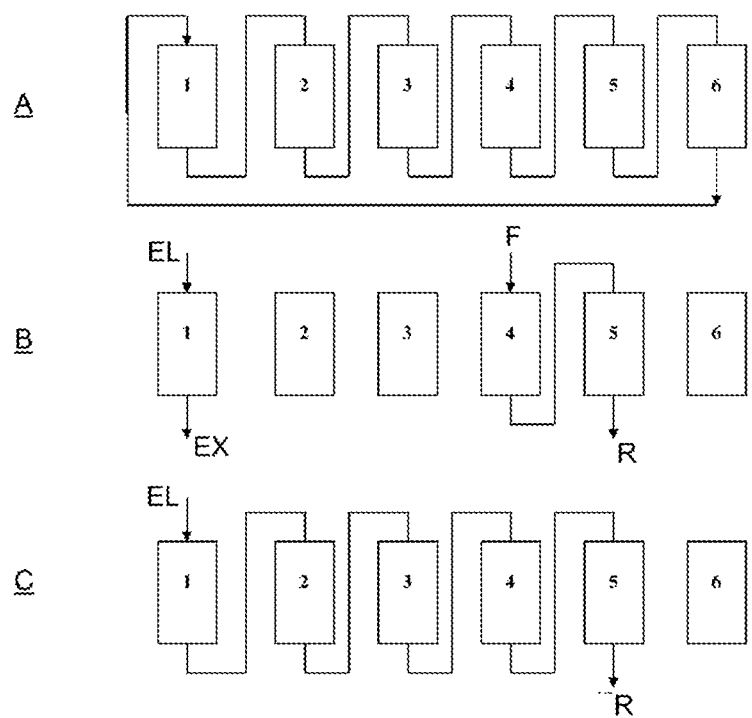

CHROMATOGRAPHIC SEPARATION OF AMMONIUM SULFATE AND 2-HYDROXY-2-METHYLPROPIONIC ACID

This application claims benefit, under U.S.C. § 119 or § 365 of PCT Application Number PCT/FR2019/050506, filed Mar. 7, 2019, and French Patent Application Number FR 1852067 filed Mar 9, 2018, these documents being incorporated herein by reference.

FIELD OF THE INVENTION

The present invention relates to a process for the chromatographic purification or separation of a starting stream containing ammonium sulfate (and possibly other salts) and 2-hydroxy-2-methylpropionic acid (and possibly other organic compounds). This purification process is particularly useful in the context of treating effluents derived from the production of methyl methacrylate from acetone cyanohydrin.

TECHNICAL BACKGROUND

Methyl methacrylate (MMA) is commonly used notably for producing organic glass made of polymethyl methacrylate (PMMA). This monomer imparts stability, strength, hardness and gloss to the polymers of which it is included in the composition.

A conventional route for synthesizing MMA is described in the book *Encyclopedia of Chemical Technology*, Kirk-Othmer, 4th edition, volume 16, pages 244-260 (2004). It is based on the use of acetone cyanohydrin (ACH) as starting material.

In the context of this synthetic route, large amounts of effluents containing ammonium sulfate may be generated.

The article *Improvement of Industrial Synthesis of Methyl Methacrylate, Application of a Wet Air Oxidation Process*, by Dario Giudici, in La Chimica e L'industria, 82:873-878 (2000), describes a treatment of such an effluent by crystallization. The crystallization purge, containing ammonium sulfate and non-ionized species, including 2-hydroxy-2-methylpropionic acid, is then treated via a wet-air oxidation (WAO) process. This is performed under drastic pressure and temperature conditions, on account of the high salt content.

U.S. Pat. No. 4,015,946 describes a separation by decantation of an aqueous phase consisting of ammonium sulfate and of a phase consisting of organic compounds. This separation is possible when the solution to be treated is saturated with ammonium sulfate, and it is based on the addition of a lactam. This process has the drawback of consuming an additional organic compound, and it can only be applied for certain concentrations of ammonium sulfate.

There is thus a need to provide a treatment of an effluent containing ammonium sulfate and 2-hydroxy-2-methylpropionic acid (and possibly other organic compounds) which does not have the above drawbacks.

SUMMARY OF THE INVENTION

The invention relates firstly to a process for the chromatographic purification of a starting stream containing ammonium sulfate and 2-hydroxy-2-methylpropionic acid, comprising:
 passage of the starting stream through a bed of stationary phase;
 elution of a raffinate enriched in ammonium sulfate and depleted in 2-hydroxy-2-methylpropionic acid; and
 elution of an extract enriched in 2-hydroxy-2-methylpropionic acid and depleted in ammonium sulfate.

In certain embodiments, the purification is performed by ion-exclusion chromatography.

In certain embodiments, the stationary phase is a cationic resin, preferably a strong cationic resin, and more preferably a strong cationic resin in $NH_4^+$ counterion form. In certain embodiments, the stationary phase consists of particles with a size Dv50 of between 200 and 350 µm.

In certain embodiments, the stationary phase is pre-equilibrated with a solution containing ammonium ions, and preferably with the starting stream.

In certain embodiments, the starting stream is at a pH of from 1 to 4 during its passage through the bed of stationary phase.

In certain embodiments, an eluent is passed through the bed of stationary phase for elution of the raffinate and elution of the extract, said eluent preferably being demineralized water or acidified demineralized water, notably at a pH of from 3 to 5, the acidified demineralized water preferably having an acid content of from 0.0005 to 5 g/L, more preferably from 0.005 to 0.02 g/L.

In certain embodiments, the process is performed at a temperature of from 20 to 85° C. and preferably from 50 to 80° C.

In certain embodiments, the process is performed on a multi-column chromatography system, preferably a simulated moving bed system, and more preferably a sequential simulated moving bed system.

In certain embodiments, the chromatography system comprises a zone 4 located between a raffinate collection line and an eluent injection line, zone 4 being traversed by a volume of mobile phase of between 0.3 and 0.55 BV, preferably between 0.4 and 0.5 BV.

In certain embodiments, the multi-column chromatography system comprises less than 12 columns, or less than 8 columns, and preferably from 4 to 6 columns.

In certain embodiments, the multi-column chromatography system comprises columns with a diameter of greater than or equal to 2 meters.

In certain embodiments, the multi-column chromatography system comprises columns with a length of between 1 and 2.5 meters.

In certain embodiments, the process is performed with a mean elution operating speed of greater than 1 m/h, or greater than 2 m/h, or greater than 4 m/h, and preferably greater than 5 m/h.

In certain embodiments, the starting stream is derived from a methyl methacrylate production process, said methyl methacrylate production process preferably comprising:
 the preparation of methacrylamide sulfate by reacting acetone cyanohydrin with sulfuric acid;
 the preparation of methyl methacrylate by reacting said methacrylamide sulfate with a mixture of water and methanol;
 collection of an acidic effluent;
 neutralization of the acidic effluent with ammonia;
 crystallization of the neutralized acidic effluent to obtain, on the one hand, ammonium sulfate crystals and, on the other hand, a crystallization purge, this crystallization purge providing said starting stream.

The present invention makes it possible to overcome the drawbacks of the prior art. It more particularly provides a treatment of an effluent containing ammonium sulfate and 2-hydroxy-2-methylpropionic acid and possibly other organic compounds, allowing the salts to be recycled into a crystallization step, for example, and allowing the organic compounds to be returned into an oxidation step, for example, as proposed in the article by D. Giudici.

The process of the invention does not consume any additional organic compound. It may also be performed with various concentrations of ammonium sulfate. There is no prerequisite minimum concentration.

The process of the invention can thus make it possible to lower the salt content in the stream to be treated, and thus to use materials that are less resistant to salts and to acidity.

BRIEF DESCRIPTION OF THE FIGURES

FIG. 1 schematically represents an SSMB chromatography system that can be used for performing the process of the invention.

DESCRIPTION OF EMBODIMENTS OF THE INVENTION

The invention is now described in greater detail and in a nonlimiting manner in the description that follows.
Production of MMA The invention is preferably applied in the context of the synthesis of MMA from ACH.

This synthesis, described in the Kirk-Othmer book, preferably comprises the following two main steps:
  reaction of ACH with sulfuric acid to form methacrylamide sulfate;
  esterification of the methacrylamide sulfate in the presence of a mixture of water and methanol to form MMA and an acidic effluent.

The first step may include two substeps: first the conversion of the ACH into an intermediate, the sulfuric monoester of 2-hydroxy-2-methylpropionamide, preferably at low temperature; and then the formation of methacrylamide sulfate from this intermediate, preferably at high temperature (for example from 100 to 140° C.).

Part of the ACH however forms various side products.

On conclusion of the second esterification step, as described in the article by D. Giudici, the desired MMA is recovered, along with an acidic effluent, which is an aqueous solution containing ammonium bisulfate, sulfuric acid and various organic compounds.

The starting stream for the chromatographic purification of the invention is advantageously obtained from this acidic effluent.

For example, as described in the article by D. Giudici, the acidic effluent may be neutralized with ammonia, which leads to the formation of ammonium sulfate. This neutralized acidic effluent may form the starting stream.

Alternatively and preferably, as described in the article by D. Giudici, a crystallization is performed starting with the neutralized acidic effluent, using a crystallizer, to recover ammonium sulfate crystals. Such a crystallization provides crystals, on the one hand, vapour, on the other hand, and finally a liquid phase, the mother liquors. One part of the mother liquors is recycled into the crystallizer, whereas the other part is removed, the latter part being referred to as the "crystallization purge". The crystallization purge is an aqueous solution notably containing ammonium sulfate and 2-hydroxy-2-methylpropionic acid (and possibly other organic compounds).

The starting stream for the chromatographic purification of the invention may be constituted directly by the crystallization purge. Alternatively, the starting stream may be obtained, for example, by diluting the crystallization purge, and/or by adding one or more products thereto.

For example, it may be useful to adjust the pH of the starting stream before subjecting it to the chromatographic purification, by adding one or more acids or bases.
Chromatographic Purification The invention envisages treatment of the starting stream by means of the following steps:
  passage of the starting stream through a bed of stationary phase (loading step);
  elution of a raffinate enriched in ammonium sulfate (and depleted in 2-hydroxy-2-methylpropionic acid); and
  elution of an extract enriched in 2-hydroxy-2-methylpropionic acid (and depleted in ammonium sulfate).

More generally, the raffinate is enriched in ionized species and depleted in non-ionized species; and the extract is enriched in non-ionized (or neutral) species and depleted in ionized species.

The term "ionized species" means species present in the starting stream in ionized form under the temperature and pH conditions used for the chromatographic purification. In the invention, the ionized species may notably comprise salts.

The term "non-ionized species" means species present in the starting stream in non-ionized form under the temperature and pH conditions used for the chromatographic purification. In the invention, the non-ionized species may notably comprise organic acids.

The term "raffinate" means the fraction obtained by elution which contains the species that are relatively the least retained by the stationary phase, and thus which are the most rapidly eluted.

The term "extract" means the fraction obtained by elution which contains the species that are relatively the most retained by the stationary phase, and thus which are the most slowly eluted.

The term fraction "enriched" in a species A and "depleted" in a species B means that the species A/species B molar concentration ratio in the fraction is greater than that in the starting stream (independently of the concentration effect or the overall dilution effect).

As described in the article by D. Giudici, the starting stream contains ammonium sulfate and 2-hydroxy-2-methylpropionic acid. Preferably, it also contains other organic compounds which constitute non-ionized species, and which may also be collected in the extract. These non-ionized species comprise, for example, MMA oligomers, and various sulfonated organic compounds. The starting stream may also contain other salts as ionized species.

The starting stream may typically contain, as mass percentages, from 5% to 95% of water, and notably, still as mass percentages: from 5% to 10% of water; or from 10% to 15% of water; or from 15% to 20% of water; or from 20% to 25% of water; or from 25% to 30% of water; or from 30% to 35% of water; or from 35% to 40% of water; or from 40% to 45% of water; or from 45% to 50% of water; or from 50% to 55% of water; or from 55% to 60% of water; or from 60% to 65% of water; or from 65% to 70% of water; or from 70% to 75% of water; or from 75% to 80% of water; or from 80% to 85% of water; or from 85% to 90% of water; or from 90% to 95% of water.

The starting stream may typically contain, as mass percentages, from 0.1% to 50% of ammonium sulfate, and notably, still as mass percentages: from 0.1% to 1% of ammonium sulfate; or from 1% to 5% of ammonium sulfate; or from 5% to 10% of ammonium sulfate; or from 10% to 15% of ammonium sulfate; or from 15% to 20% of ammonium sulfate; or from 20% to 25% of ammonium sulfate; or from 25% to 30% of ammonium sulfate; or from 30% to 35% of ammonium sulfate; or from 35% to 40% of ammonium sulfate; or from 40% to 45% of ammonium sulfate; or from 45% to 50% of ammonium sulfate.

The starting stream may typically contain, as mass percentages, from 0.1% to 50% of 2-hydroxy-2-methylpropionic acid, and notably, still as mass percentages: from 0.1% to 0.5% of 2-hydroxy-2-methylpropionic acid; or from 0.5% to 1% of 2-hydroxy-2-methylpropionic acid; or from 1% to 2% of 2-hydroxy-2-methylpropionic acid; or from 2% to 3% of 2-hydroxy-2-methylpropionic acid; or from 3% to 4% of 2-hydroxy-2-methylpropionic acid; or from 4% to 5% of 2-hydroxy-2-methylpropionic acid; or from 5% to 10% of 2-hydroxy-2-methylpropionic acid; or from 10% to 15% of 2-hydroxy-2-methylpropionic acid; or from 15% to 30% of 2-hydroxy-2-methylpropionic acid; or from 30% to 50% of 2-hydroxy-2-methylpropionic acid.

The chromatographic purification of the invention is preferably based on an ion exclusion mechanism, and not on an ion exchange mechanism. According to this ion exclusion mechanism, salts and other charged molecules have a tendency to be excluded from the stationary phase, whereas neutral molecules have a tendency to interact with the stationary phase and to be retained thereby.

The stationary phase preferably remains essentially in the same ionic form during the loading and elution steps. Furthermore, the process of the invention is preferably free of a step of regenerating the stationary phase after elution.

The pH of the starting stream may notably be from 0.5 to 6, preferably from 1 to 5, more preferably from 1 to 4, during the loading step.

The process of the invention may comprise one or more pretreatment steps as a function of the variability of the product to be treated. These may be steps of filtration, of separation by ion exchange or of passage through a chelating resin.

Alternatively, in preferred embodiments, the invention envisages a single passage through a stationary phase, as described in greater detail hereinbelow. Thus, in preferred embodiments, no passage through a stationary phase which is an anionic resin is envisaged, upstream or downstream.

The stationary phase used may notably be a cationic resin. Preferably, it is a strong cationic resin, and more preferably a strong cationic resin (for example bearing sulfonic functional groups) converted into $NH_4^+$ form. Several cationic chromatography resins may be suitable for this separation: XA resin from Novasep, such as XA2014/28K, the resins Dowex from Dow, Diaion from Mitsubishi, or the cationic chromatography resins from Lanxess, Finex or Purolite.

Preferably, the stationary phase is in the form of particles with a size Dv50 of from 200 to 350 μm.

The term "Dv50" denotes the 50th percentile of the particle size distribution, that is to say that 50% of the particles have a size less than the Dv50 and 50% have a size greater than the Dv50. It is the median of the volumetric distribution of the resin particles.

The Dv50 value may be determined by laser scattering particle size analysis. In certain cases, the individual particles may have a tendency toward aggregation, in which case their size should be determined by electron microscopy, since the apparent size measured by laser scattering particle size analysis is then larger than the real particle size.

The process of the invention may comprise a preliminary step (before loading) of equilibrating the stationary phase, notably: with a solution containing ammonium ions (for example an ammonium chloride solution with a mass titer of from 5% to 20%, for example about 10%); or else, preferably, with the starting stream itself having, for example, a mass titer of about 20%. In such a case, part of the starting stream is consumed for the preliminary equilibration step before the actual purification takes place.

The temperature at which the process is performed is preferably from 20 to 85° C. It is possible to envisage different temperatures for the different steps, but, preferably, the temperature is substantially constant during the process.

The temperature may notably be from 20 to 25° C.; or from 25 to 30° C.; or from 30 to 35° C.; or from 35 to 40° C.; or from 40 to 45° C.; or from 45 to 50° C.; or from 50 to 55° C.; or from 55 to 60° C.; or from 60 to 65° C.; or from 65 to 70° C.; or from 70 to 75° C.; or from 75 to 80° C.; or from 80 to 85° C.

A temperature range from 50 to 80° C. and notably from 60 to 70° C. may be preferred.

The elution steps are performed by passing an eluent through the bed of stationary phase. The eluent may be different for the elution of the raffinate or of the extract. An eluent with a composition gradient may also be used. However, preferably, the same eluent having a given composition is used for all of the elutions.

The eluent may simply be water, preferably demineralized water, without adjustment of the pH. The demineralized water may typically have a pH from 5 to 7.

Alternatively, the eluent may be water (preferably demineralized water as described above) which is acidified, i.e. an aqueous solution of acid in water (preferably demineralized water as described above). Preferably, the acid used is sulfuric acid. Other possibilities are: nitric acid, hydrochloric acid, citric acid and mixtures of these acids.

The concentration of the acid (notably sulfuric acid) in the aqueous solution may notably be less than or equal to 5 g/L, preferably less than or equal to 2 g/L, more preferably less than or equal to 1 g/L, more preferably less than or equal to 0.5 g/L and more preferably less than or equal to 0.2 g/L. Ranges of from 0.0005 to 0.2 g/L, preferably from 0.001 to 0.1 g/L, preferably from 0.002 to 0.05 g/L and more preferably from 0.005 to 0.02 g/L are notably suitable.

The pH of the acidified water used as eluent may notably be from 1 to 2; or from 2 to 3; or from 3 to 4; or from 4 to 5; or from 5 to 6. A pH of from 3.5 to 4.5, and notably of about 4, may be particularly desirable.

The mass ratio of the total amount of eluent consumed to the total amount of starting stream may notably be from 0.5 to 1; or from 1 to 1.5; or from 1.5 to 2; or from 2 to 3; or from 3 to 4; or from 4 to 5; or from 5 to 6; or from 6 to 7; or from 7 to 8; or from 8 to 9; or from 9 to 10; or from 10 to 12; or from 12 to 15; or from 15 to 20. Ranges from 2 to 8 and notably from 3 to 6 are particularly preferred.

When the process is a cyclic process, in which the steps of injection of the starting stream and of elution are performed repeatedly in the same column (typically forming part of a multi-column system), the above volumes are the volumes observed over one cycle.

The mean operating speed of the eluent through the bed of stationary phase, both for the elution of the extract and for the elution of the raffinate, is preferably greater than 1 m/h, or greater than 2 m/h, or greater than 4 m/h, and preferably greater than 5 m/h. This mean operating speed corresponds to the mean volume flow rate divided by the mean cross-sectional area of the bed of stationary phase.

Preferably, the total mass amount of salts in the extract is less than or equal to 30% of the total mass amount of salts in the starting stream, more preferably less than or equal to 20%, or to 15%, or to 10%, or to 5%. Ranges from 1% to 15% and from 1.5% to 10% are particularly preferred.

Preferably, the mass amount of ammonium sulfate in the extract is less than or equal to 30% of the mass amount of ammonium sulfate in the starting stream, more preferably less than or equal to 20%, or to 15%, or to 10%, or to 5%. Ranges from 1% to 15% and from 1.5% to 10% are particularly preferred.

Preferably, the mass amount of 2-hydroxy-2-methylpropionic acid in the extract is greater than or equal to 80% of the mass amount of 2-hydroxy-2-methylpropionic acid in the starting stream, more preferably greater than or equal to 87%, preferably greater than or equal to 90%.

In certain embodiments, the elution peak of the ionized species, and notably of ammonium sulfate (concentration maximum of the ionized species in the collected stream) is between 0.3 and 0.6 BV, preferably between 0.4 and 0.55 BV; for example, it may be approximately 0.47 BV.

In certain embodiments, the elution peak of the non-ionized species, and notably of 2-hydroxy-2-methylpropionic acid (concentration maximum of the non-ionized species in the collected stream) is between 0.4 and 0.9 BV, preferably between 0.5 and 0.7 BV; for example, it may be approximately 0.67 BV.

The unit BV (bed volume) corresponds to the volume of the bed of stationary phase.

Chromatographic System

The process of the invention may be performed in a one-column chromatographic system or, preferably, in a multi-column chromatographic system. More preferably, the chromatographic system comprises from 4 to 10 columns.

Preferably, the process of the invention is performed continuously.

Preferably, the process according to the invention is a periodic accumulation chromatographic process.

The term "accumulation process" means a chromatographic process in which the injection of the mixture to be separated (starting stream) is intercalated into or added to a nonzero concentration profile going from the outlet to the inlet of a column.

Examples of such accumulation processes are the AMB, SMB, VariCol, Powerfeed, ModiCon, iSMB or SSMB processes.

The simulated moving bed (or SMB) process is a continuous multi-column process, the injection of mixture to be separated being performed on the whole of a cycle.

The SMB process may notably be a four-zone SMB process. In this case, the system includes a set of columns mounted in series and in a closed loop, the outlet of one column being connected to the inlet of a following column. The system comprises at least one line for injecting mixture to be separated, a raffinate collection line, an eluent injection line and an extract collection line. The injection lines (for starting stream and eluent) and the fraction collection lines move periodically and synchronously (synchronous sequencing) within the loop in the direction of flow of the fluid circulating through the loop. The duration between two shifts of all of the injection and collection lines of a column corresponds to one period; after one cycle, all the points have returned to their initial position, the system having cyclic functioning. A cycle includes as many periods as there are columns.

An AMB (actual moving bed) system has similar functioning to an SMB system. However, instead of moving the points of injection of the feed stream and of the eluent, and also the collection points, by means of a valve system, a set of adsorption units (columns) are physically moved relative to the feed and collection points. Once again, the functioning makes it possible to simulate a continuous counter-current moving bed.

The process according to the invention may be a process with continuous injection of the mixture to be separated (i.e. a process in which the injection of the mixture to be separated is a continuous stream). The injection of the mixture to be separated is then performed over the entire duration of the cycle. The process according to the invention may also be a process with quasi-continuous injection of the mixture to be separated.

Alternatively, the process according to the invention may be a process in which the injection of the mixture to be separated (starting stream) is discontinuous. In these processes, the injection of the mixture to be separated is not performed on the whole of a cycle but over a total duration of less than one cycle. A process with discontinuous injection of mixture to be separated that may be mentioned is the iSMB (improved simulated moving bed) process described in EP 0342629 and U.S. Pat. No. 5,064,539, to which reference is expressly made. In this process, in one step, the system functions as a closed loop, without injection or collection of product.

The sequential SMB process or SSMB (sequential simulated moving bed) process is another preferred example. An SSMB system cuts the introductions and collections of the streams into sub-sequences applied periodically. An SSMB system is described, for example, in WO 2015/104464.

Preferably, the process according to the invention is a process of SSMB type.

When the chromatographic system used is a multi-column system, and preferably when the process is an accumulation process, the chromatographic system preferably comprises zones 1, 2, 3 and 4: zone 1 is located between an eluent injection line and an extract collection line; zone 2 is located between the extract collection line and a line for injecting the mixture to be separated; zone 3 is located between the line for injecting the mixture to be separated and a raffinate collection line; and zone 4 is located between said raffinate collection line and the eluent injection line.

A possible example of an SSMB system that may be used in the invention is represented with reference to FIG. 1. In this example, six cells or columns are used. This system may be operated with cyclic functioning in four phases.

Phase 1 (part A of the figure): loop phase, during which continuous circulation is maintained in a closed loop on all the cells placed in series, to move the interstitial volume from one cell to the next, without injection of eluent. A person skilled in the art observes that the volume of mobile phase moved in this phase contributes to zones 1, 2, 3 and 4.

Phase 2 (part B of the figure): loading/load injection. The stream (F) load is injected into the top of the fourth cell. Simultaneously, a substantially identical volume of raffinate (R) is collected at the outlet of the fifth cell. Cells 4 and 5 constitute here zone 3. Cells 2 and 3 constitute the zone for separation between extract and injection of load. They constitute here zone 2. A person skilled in the art observes that the volume of mobile phase moved in this phase contributes to zone 3.

Phase 3 (part B of the figure): elution of the extract. The eluent (EL) is injected onto the first cell to elute the extract (EX), which is collected in a substantially identical volume at the bottom of the first cell. Cell 1 constitutes here zone 1. A person skilled in the art observes that the volume of mobile phase moved in this phase contributes to zone 1.

Phases 2 and 3 are preferably performed simultaneously to increase the productivity of the system.

Phase 4 (part C of the figure): elution of the raffinate. The eluent (EL) is injected into the top of the first cell, and the raffinate (R) is collected in a substantially identical volume at the outlet of the fifth cell. Cell 6 is here a buffer cell for ensuring separation between the tail of the extract and the head of the raffinate. It constitutes zone 4. This zone may be omitted in the case where the desired degree of purity and/or yield is relatively limited. A person skilled in the art observes that the volume of mobile phase moved in this phase contributes to zones 1, 2 and 3.

In the case of a multi-column process with zones identified between the inlet and outlet lines, the term "volume of mobile phase" denotes the volume of fluid which enters a zone. This fluid may be different from the eluent in the strict sense, but it contributes toward the movement of the products in each column of the zone. It is thus referred to as the volume of mobile phase associated with each zone.

In the case of an SSMB process, the volume of zone 4 corresponds to the volume of mobile phase moved during phase 1 (part 1 of the figure). When the process is a cyclic process, in which the steps of injection of the starting stream and of elution are performed repeatedly in the same column (typically belonging to a multi-column system), the above volumes are the volumes observed over one cycle. In the case of the SSMB, SMB, VariCol, AMB and iSMB processes, the volume of mobile phase used in zone 4 is preferably between 0.3 and 0.55 BV, more preferably between 0.4 and 0.5 BV.

These phases are operated in the order, in a preferred embodiment, from 1 to 4. Their sequence constitutes a full sequence.

Each sequence (phases 1 to 4) is repeated six times, shifting the cell inlets and outlets by incrementation of the cell number, from left to right in the system: the load is thus injected into the top of cell 1 in sequence 1, and then into the top of cell 2 in sequence 2, etc.

A full production cycle is achieved after completing the six successive sequences, when the point of injection of the load, initially at the inlet of cell 1, returns once again to the inlet of cell 1.

A description of the SSMB system has been given in the foregoing with reference to the case where the cells correspond to columns. This is not limiting, and the invention also applies to systems in which the cells, or compartments, are column parts.

Moreover, the number of columns present in zones 1, 2, 3 and 4 may vary as a function of the desired separation quality. Systems of the same type may thus be designed with one cell, two cells, three cells, four cells and up to 12 cells or more.

EXAMPLE

The example that follows illustrates the invention without limiting it.

A synthetic mixture containing 20% by mass of ammonium sulfate and 2.5% by mass of 2-hydroxy-2-methylpropionic acid was prepared.

Tests were performed with a strong cationic resin. In each test, 0.1 BV of the synthetic mixture is injected onto the resin and then eluted.

The cationic resin is the following:

Applexion® XA 2014/28 K cationic resin, converted beforehand into $NH_4^+$ form with an $NH_4Cl$ solution at 10% by mass. The resin has a total capacity of 1.6 eq/L and a humidity of 55% to 59% by mass.

Two tests were performed using this resin in a column 2.5 cm in diameter and 97.1 cm in length. The two tests were performed at a temperature of 65° C. and with an elution flow rate of 20 mL/min. The injection volume of the synthetic product is 5 mL. In test 1, the eluent was demineralized water; and in test 2, the eluent was water acidified with sulfuric acid at 0.005 g/L.

Samples were taken every 0.05 BV between 0.25 BV and 0.9 BV of elution. These samples were analyzed by conductimetry with a Mettler-Toledo 5230 conductimeter, by HPLC chromatography in order to monitor the elution of the sulfate and ammonium ions and also the concentration of 2-hydroxy-2-methylpropionic acid, and by Brix measurement.

The characteristics of the HPLC ion chromatography (Dionex) are the following:

Measurement of the cations:
  Precolumn: IONPAC CG 12A 2 mm;
  Column: IONPAC CS 12A 2 mm;
  Mobile phase: degassed 20 mM hydroxymethanesulfonic acid;
  Flow rate: 0.25 mL/min;

Measurement of the anions:
  Precolumn: IONPAC AG 15 2 mm;
  Column: IONPAC AS 15 2 mm;
  Mobile phase: ultrapure water connected to a KOH generator—gradient 11 to 71 mM;
  Flow rate: 0.3 mL/min;

The characteristics of the HPLC chromatography used for measuring the 2-hydroxy-2-methylpropionic acid concentration are the following:

HPLC column: Aminex HPX 87H;
Mobile phase: 5 mM $H_2SO_4$;
Detection: Refractive Index;
Column temperature: 60° C.;
Detector temperature: 55° C.;
Injection volume: 20 µL;
Flow rate: 1 mL/min;
Analysis time: 35 min;
2-Hydroxy-2-methylpropionic acid retention time: 7.8 min;
Quantification: concentration expressed in g/L.

For test 1, the separation profiles of the various species present in the synthetic product make it possible to identify a first elution peak at 0.47 BV, corresponding to ammonium sulfate, and a second elution peak between 0.62 and 0.67 BV corresponding to 2-hydroxy-2-methylpropionic acid.

A degree of elimination of the ammonium sulfate of 98.5% is also observed, i.e. 98.5% of the ammonium sulfate initially present in the synthetic product is eluted in the raffinate.

A degree of recovery of the 2-hydroxy-2-methylpropionic acid of 87% is also observed, i.e. 87% of the 2-hydroxy-2-methylpropionic acid initially present in the synthetic product is eluted in the extract.

For test 2, the separation profiles of the various species present in the synthetic product make it possible to identify a first elution peak at 0.47 BV, corresponding to ammonium sulfate, and a second elution peak at 0.67 BV corresponding to 2-hydroxy-2-methylpropionic acid.

A degree of elimination of the ammonium sulfate of 98.5% is also observed, i.e. 98.5% of the ammonium sulfate initially present in the synthetic product is eluted in the raffinate.

A degree of recovery of the 2-hydroxy-2-methylpropionic acid of 91% is also observed, i.e. 91% of the 2-hydroxy-2-methylpropionic acid initially present in the synthetic product is eluted in the extract.

These tests show that separation is possible and naturally the retention volume values may vary from one test to another or from one cationic stationary phase to another. However, the difference in retention volumes is sufficient to perform purification on an industrial scale.

Starting from this example, and with the aid of chromatographic simulation software, for example using the methods described in the manual *Preparative Chromatography of Fine Chemicals and Pharmaceutical Agents*, Henner Schmidt-Traub, Wiley-VCH, ISBN-13 978-3-527-30643-5, it is possible to deduce a ratio between the amount of eluent and the amount of product injected into the chromatography column of between 1.5 and 5.4. This volume ratio changes as a function of the length and number of columns and also of the composition of the load to be treated, if, for example, the 2-hydroxy-2-methylpropionic acid content is between 5% and 10% or between 1% and 5%. The calculations made it possible to show that purification can be performed on a wide range of initial compositions.

The process according to the invention may advantageously be performed in an SSMB system of 4 to 6 columns with a column length of between 1.5 and 2.5 m, depending on the type of eluent used and the operating elution rate which will be greater than 1 m/h, or greater than 2 m/h, or greater than 4 m/h, and preferably greater than 5 m/h. It is, however, determined that it is possible to use a column length of, for example, from 0.5 to 1 m if a larger number of columns is used, for example 12 or 24. These calculations show that a column diameter of greater than two meters makes it possible to process a stream of several cubic meters per hour. An important element obtained during these calculations is the constraint on the volume of zone 4 to be used in order to demineralize the 2-hydroxy-2-methylpropionic acid, which is between 0.3 and 0.55 BV, preferably between 0.4 and 0.5 BV.

The invention claimed is:

1. A process for the chromatographic purification of a starting stream containing ammonium sulfate and 2-hydroxy-2-methylpropionic acid, comprising:
    passing said starting stream through a bed of stationary phase;
    elution of a raffinate enriched in ammonium sulphate and depleted in 2-hydroxy-2-methylpropionic acid; and
    elution of an extract enriched in 2-hydroxy-2-methylpropionic acid and depleted in ammonium sulphate.

2. The process as claimed in claim 1, wherein the purification is performed by ion-exclusion chromatography.

3. The process as claimed in claim 1, wherein the stationary phase is a cationic resin.

4. The process as claimed in claim 1, wherein the stationary phase consists of particles with a size Dv50 of between 200 and 350 µm.

5. The process as claimed in claim 1, wherein the stationary phase is pre-equilibrated with a solution containing ammonium ions.

6. The process as claimed in claim 1, wherein the starting stream is at a pH of from 1 to 4 during its passage through the bed of stationary phase.

7. The process as claimed in claim 1, wherein an eluent is passed through the bed of stationary phase for the elution of the raffinate and the elution of the extract, said eluent being demineralized water or acidified demineralized water, at a pH of from 3 to 5, the acidified demineralized water having an acid content of 0.0005 to 5 g/L.

8. The process as claimed in claim 1, which is performed at a temperature of from 20 to 85° C.

9. The process as claimed in claim 1, performed on a multi-column chromatographic system.

10. The process as claimed in claim 9, wherein the chromatographic system comprises a zone 4 located between a raffinate collection line and an eluent injection line, zone 4 being traversed by a volume of mobile phase of between 0.3 and 0.55 BV.

11. The process as claimed in claim 9, wherein the multi-column chromatographic system comprises less than 12 columns.

12. The process as claimed in claim 9, wherein the multi-column chromatographic system comprises columns with a diameter of greater than or equal to 2 meters.

13. The process as claimed in claim 9, wherein the multi-column chromatographic system comprises columns having a length of between 1 and 2.5 meters.

14. The process as claimed in claim 1, which is performed with a mean elution operating speed of greater than 1 m/h.

15. The process as claimed in claim 1, wherein the starting stream is derived from a methyl methacrylate production process, said methyl methacrylate production process comprising the steps of:
    reacting acetone cyanohydrin with sulfuric acid to prepare methacrylamide sulfate;
    reacting said methacrylamide sulfate with a mixture of water and methanol to prepare methyl methacrylate;
    collecting an acidic effluent;
    neutralizing the acidic effluent with ammonia; and
    crystallizing the neutralized acid effluent to obtain ammonium sulfate crystals and a crystallization purge, this crystallization purge providing said starting stream.

16. The process as claimed in claim 3, wherein the stationary phase is a strong cationic resin in $NH_4^+$ counterion form.

17. The process as claimed in claim 1, wherein the stationary phase is pre-equilibrated with the starting stream.

18. The process as claimed in claim 8, which is performed at a temperature of from 50 to 80° C.

19. The process as claimed in claim 9, performed on a multi-column chromatography system selected from the group consisting of a simulated moving bed system, and a sequential simulated moving bed system.

* * * * *